US00PP35323P2

(12) United States Plant Patent
Brown

(10) Patent No.: US PP35,323 P2
(45) Date of Patent: Aug. 15, 2023

(54) ***KNIPHOFIA* PLANT NAMED 'KLEKN22193'**

(50) Latin Name: *Kniphofia uvaria*
Varietal Denomination: KLEKN22193

(71) Applicant: KLEMM + SOHN GMBH & CO. KG, Stuttgart (DE)

(72) Inventor: Graham N. Brown, Bowral (AU)

(73) Assignee: KLEMM+SOHN GMBH & CO. KG, Stuttgart (DE)

( * ) Notice: Subject to any disclaimer, the term of this patent is extended or adjusted under 35 U.S.C. 154(b) by 0 days.

(21) Appl. No.: 17/935,659

(22) Filed: Sep. 27, 2022

(51) Int. Cl.
*A01H 5/02* (2018.01)
*A01H 6/00* (2018.01)

(52) U.S. Cl.
USPC ..... Plt./443
CPC ..... *A01H 6/00* (2018.05)

(58) Field of Classification Search
USPC ..... Plt./443
CPC ..... A01H 5/02
See application file for complete search history.

*Primary Examiner* — Kent L Bell
(74) *Attorney, Agent, or Firm* — Weatherly IP Solutions, LLC; James M. Weatherly

(57) ABSTRACT

A new *Kniphofia* plant particularly distinguished by a short plant height and early flowering, is disclosed.

1 Drawing Sheet

Genus and species: *Kniphofia uvaria.*
Variety denomination: 'KLEKN22193'.

BACKGROUND OF THE NEW PLANT

The present invention comprises a new and distinct variety of *Kniphofia*, botanically known as *Kniphofia uvaria*, and hereinafter referred to by the variety name 'KLEKN22193'. 'KLEKN22193' originated from a hand pollination conducted in December 2015 in Cobbitty, New South Wales, Australia between the proprietary female *Kniphofia* variety 'x14.1.1' (unpatented), and the proprietary male *Kniphofia* variety 'x14.1.2' (unpatented).

The seeds from the cross were sown and plants were grown for evaluation, where an individual plant designated 'KLEKN22193' was selected from the group of plants in Cobbitty, New South Wales, Australia in December 2016.

In December 2016, 'KLEKN22193' was first vegetatively propagated by stem cuttings in Cobbitty, New South Wales, Australia. 'KLEKN22193' was found to reproduce true to type in successive generations of asexual propagation via vegetative stem cuttings.

SUMMARY

The following are the most outstanding and distinguishing characteristics of this new variety when grown under normal horticultural practices in Stuttgart, Germany.

1. A short plant height; and
2. Early flowering.

DESCRIPTION OF THE PHOTOGRAPH

This new *Kniphofia* plant is illustrated by the accompanying photograph which shows the plant's overall plant habit including form, buds, foliage, and flowers. The photograph is of a plant approximately 20 weeks old grown indoors in Stuttgart, Germany in June 2022. The colors shown are as true as can be reasonably obtained by conventional photographic procedures.

DESCRIPTION OF THE NEW VARIETY

The following detailed descriptions set forth the distinctive characteristics of 'KLEKN22193'. The data which define these characteristics were collected from asexual reproductions carried out in Stuttgart, Germany. Data was collected on five-month-old plants grown in a greenhouse in July of 2022. Color references are to The R.H.S. Colour Chart of The Royal Horticultural Society of London (R.H.S.), 5$^{th}$ edition (2007).

Classification:
- *Family.*—Asphodelaceae.
- *Botanical.*—*Kniphofia uvaria.*
- *Common.*—*Kniphofia.*
- *Designation.*—'KLEKN22193'.

Parentage:
- *Female parent.*—'x14.1.1' (unpatented).
- *Male parent.*—'x14.1.2' (unpatented).

Plant:
- *Form.*—V-shaped.
- *Habit.*—Upright.
- *Plant height.*—40.0 cm.
- *Plant width.*—30.0 cm.
- *Flowering habit.*—Perennial.
- *Time to produce a finished flowering plant.*—18 weeks.
- *Propagation type.*—Tissue culture, vegetative (rhizomes, division).
- *Time to initiate roots.*—Unknown.
- *Root description.*—Fibrous from base of rhizomes, light brown.

Leaves:
- *Arrangement.*—Basal rosette.
- *Length.*—20.0 cm to 35.0 cm.
- *Width.*—0.2 cm to 0.4 cm.
- *Shape.*—Strap-like, keeled.
- *Apex.*—Acuminate.
- *Base.*—Clasping, truncate.

*Margin*.—Entire.
*Texture*.—Upper surface: Glabrous. Lower surface: Smooth.
*Color*.—Immature leaf: Upper surface: RHS 143A. Lower surface: RHS 143C. Mature leaf: Upper surface: RHS 137B. Lower surface: RHS 138A.
*Venation pattern*.—Parallel.
*Venation color*.—Upper surface: RHS 143A. Lower surface: RHS 143C.
*Petiole*.—Absent.

Flower bud:
*Shape*.—Conical (the whole immature inflorescence) (height: 2.5 cm and width: 2.0 cm); single bud cylindrical.
*Height*.—0.4 cm to 1.0 cm.
*Width*.—0.1 cm to 0.2 cm.
*Color*.—RHS 37D, RHS 144B, RHS 3B from top to base.
*Texture*.—Smooth, waxy.

Flowers:
*Type*.—Terete; six tepals forming a tubular corolla; perfect; actinomorphic.
*Number of inflorescences per plant*.—30.
*Number of flowers per inflorescence*.—180.
*Type*.—Scapose.
*Shape*.—Spike-like.
*Inflorescence length*.—70.0 cm with 35 flowers.
*Inflorescence diameter*.—7.0 cm.
*Lastingness of the inflorescence*.—2 to 4 weeks depending on the temperature.
*Quantity of flowers per pedicel*.—1.
*Flowering season*.—June to October.
*Lastingness of individual flowers on the plant*.—2 to 4 weeks.
*Fragrance*.—Absent.
*Corolla*.—Length: 2.0 cm to 2.2 cm. Width: 0.3 cm to 0.5 cm. Shape: Tubular, with swollen subacute apex. Tepals: 6 lobed fused tepals. Length: 0.1 cm to 0.2 cm. Width: 0.1 cm to 0.2 cm. Shape: Ovate. Apex: Acute. Base: Fused. Margin: Entire. Color, immature: Upper surface: RHS 9B. Lower surface: RHS 8B. Color, mature: Upper surface: RHS 8A. Lower surface: RHS 5C. Texture: Upper surface: Smooth. Lower surface: Smooth.
*Peduncle*.—Length: 65.0 cm. Diameter: 0.6 cm. Color: RHS 143A. Texture: Smooth.
*Pedicel*.—Length: 0.2 cm to 0.3 cm. Diameter: Less than 0.1 cm. Color: RHS 150C. Texture: Smooth.

Bracts:
*Quantity per flower*.—1.
*Length*.—0.3 cm to 0.7 cm.
*Width*.—0.1 cm to 0.2 cm.
*Shape*.—Lanceolate.
*Apex*.—Acute.
*Base*.—Truncate.
*Margin*.—Entire.
*Surface texture*.—Upper surface: Hyaline, glabrous. Lower surface: Hyaline, glabrous.
*Color*.—Upper surface: RHS 161D. Lower surface: RHS 161D.

Reproductive organs:
*Androecium*.—Quantity of stamens per floret: 6. Filament length: 1.5 cm to 2.0 cm. Filament color: RHS 4D. Anther color: RHS 9A. Anther shape: Convex, cymbiform. Anther length: 0.2 cm. Pollen amount: Moderate. Pollen color: RHS 9A.
*Gynoecium*.—Quantity of pistils per floret: 1. Pistil length: 2.0 cm to 2.2 cm. Style length: 1.8 cm to 2.0 cm. Style color: RHS 7 D. Stigma shape: Flattened, round. Stigma color: RHS 7D. Ovary color: RHS 145A.

Fruit and seed set: Does not produce seed.

Disease and insect resistance: No particular disease or insect resistance observed.

COMPARISON WITH PARENTAL LINES AND KNOWN VARIETY

'KLEKN22193' is distinguished from its parents as described in Table 1.

TABLE 1

Comparison with Parental Lines

| Trait | Variety 'KLEKN22193' | Female parent 'X14.1.1' | Male Parent 'x14.1.2' |
|---|---|---|---|
| Plant height | Short | Medium | Short |
| Early Flowering | Early | Medium | Medium |

'KLEKN22193' is most similar to the commercial *Kniphofia* variety 'POCO' (unpatented). Differences between the varieties are described in Table 2.

TABLE 2

Comparison with Similar Variety

| Trait | Variety 'KLEKN22193' | Similar Variety 'POCO' |
|---|---|---|
| Early flowering | Earlier flowering than 'POCO' | Later than 'KLEKN22193' |

I claim:

1. A new and distinct cultivar of *Kniphofia* plant named 'KLEKN22193' as described and illustrated herein.

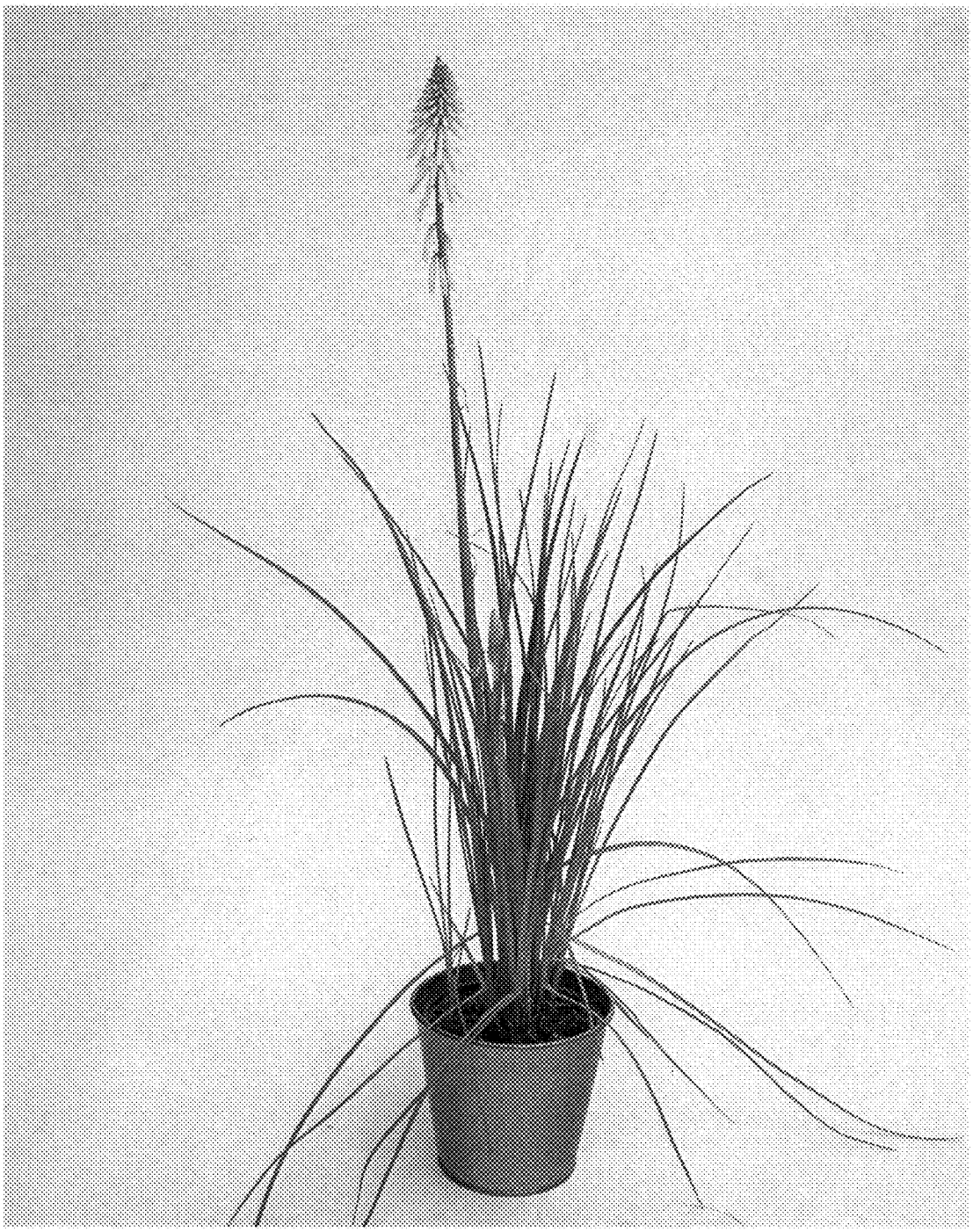

* * * * *